United States Patent [19]

Virta

[11] Patent Number: 5,267,293
[45] Date of Patent: Nov. 30, 1993

[54] METHOD AND APPARATUS FOR PANORAMIC RADIOGRAGRAPHY

[75] Inventor: Arto Virta, Helsinki, Finland
[73] Assignee: Planmeca Oy, Finland
[21] Appl. No.: 878,159
[22] Filed: May 4, 1992

[30] Foreign Application Priority Data

May 6, 1991 [FI] Finland .................................. 912180

[51] Int. Cl.$^5$ .............................................. A61B 6/14
[52] U.S. Cl. .......................................... 378/40; 378/38
[58] Field of Search .............................. 378/38, 39, 40

[56] References Cited

U.S. PATENT DOCUMENTS

| | | | |
|---|---|---|---|
| 4,242,585 | 12/1980 | Yamano | 378/39 |
| 4,599,739 | 7/1986 | Nishikawa . | |
| 4,675,888 | 6/1987 | Gastrin . | |
| 4,783,793 | 11/1988 | Virta et al. | 378/40 |
| 4,847,881 | 7/1989 | Heubeck | 378/40 |
| 4,852,134 | 7/1989 | Kinanen et al. | 378/39 |
| 4,856,038 | 8/1989 | Guenther et al. | 378/40 |
| 4,985,907 | 1/1991 | Moteni . | |
| 5,093,852 | 3/1992 | Nishikawa et al. | 378/39 |

FOREIGN PATENT DOCUMENTS

840044 7/1985 Finland .
892130 11/1989 Finland .
895295 9/1990 Finland .

OTHER PUBLICATIONS

Finnish Official Action, The National Board of Patents and Registration, Dec. 12, 1991.
Israel Chilvarquer et al., "A New Technique for Imaging the Temporomandibular Joint With a Panoramic X-Ray Machine", Oral Surgery, pp. 626–630, May 1988.

Primary Examiner—Craig E. Church
Attorney, Agent, or Firm—Jones & Askew

[57] ABSTRACT

The invention concerns a method and apparatus for narrow-beam tomography in which a narrow x-ray beam (X) emitted from an x-ray source (12) is aimed to pass through the object area to be radiographed onto a transferrable x-ray film (F). The object area to be imaged in the patient (P) is kept stationary in a certain preset position, while the x-ray source (12) is rotated about a virtual axis of rotation ($R_0$) and the film cassette (14) is simultaneously transferred. In the first imaging mode for the panoramic radiography of the dental arch (L), the patient (P) is supported by patient positioning means (20 . . . 30) so that the sharply imaging plane is located between the virtual axis of rotation and the film plane. In addition to said first imaging mode, the panoramic x-ray apparatus is adjustable for a specific mandibular joint imaging mode in which the patient is supported in the panoramic x-ray apparatus using said patient positioning means (20 . . . 30). The speeds ($v_R$, $v_1$) of the rotating motor (31) and the film transfer motor (32) in a frame part (15) supporting the x-ray source (12) and the film cassette (14) are varied, or alternatively, the profiles of said speeds are set so that the shape of the sharply-imaging layers ($P_1-P_1, P_2-P_2$) is appropriately contoured so as to make the mandibular joints (K) coincide with the imaged layer irrespective of the position of the patient (P) in the medial-sagittal plane (MS).

7 Claims, 7 Drawing Sheets

METHOD AND APPARATUS FOR PANORAMIC RADIOGRAGRAPHY

The invention relates to a method of narrow-beam panoramic radiography, said method utilizing an x-ray source whose narrow x-ray beam is aimed to pass through the object area to be radiographed onto a movable x-ray film, in which method the object area to be radiographed in the patient is kept stationary in a certain preset position, while the x-ray source is rotated about a virtual, preferably vertical axis of rotation and a film cassette is simultaneously moved, and in which method according to its first operating mode the patient is supported by patient positioning means for exposing panoramic radiographic images of the dental arch so that the sharply imaging plane is located between the virtual axis of rotation of the x-ray beam and the film plane, and in which method in addition to above-described first operating mode the panoramic x-ray apparatus is set to a specific exposure mode for imaging the dental arch and the patient is positioned in the panoramic x-ray apparatus with the help of above-mentioned patient positioning means.

Furthermore, the invention concerns a panoramic tomographic apparatus for dental radiography, said apparatus comprising a body frame part to which is mounted another frame part, pivotal in bearings about a vertical axis, whose one end is carrying an x-ray tube and the other end carrying a film cassette, capable of housing an x-ray film, and the space between said x-ray tube and said film cassette being able to accommodate the object area to be radiographed in the patient, and said apparatus further comprising actuating means, capable of rotating said pivotally mounted frame part in the horizontal plane and transferring said film cassette simultaneously for exposing a panoramic radiographic image, and said apparatus further comprising patient positioning means which are transferrable manually or by a motor in the forward-backward direction for positioning the patient in such a position that in the specific mandibular joint imaging mode permits the imaging of the mandibular joint.

Most panoramic radiographic equipment intended for dental radiography are by their function and construction so designed that their x-ray source is rotated about the patient's skull, whereby the dental arch can be imaged onto a movable film in a planar development of the dental arch. In order to achieve a sharp image of the object area onto the film with a simultaneous desired "blurring" of the structures situated along the beam axis in the front or rear of the object area, the film travel speed orthogonally to the exposing beam must be equal to the sweep velocity of the beam at the imaged object area multiplied by the magnification. The magnification is set by the ratio of distance from the focal point to the film plane to the distance from the focal point to the object area being imaged. The thickness of sharply imaging layer is linearly proportional to the distance of the virtual axis of rotation from the film plane and inversely proportional to the magnification and the width of the x-ray beam. Only the mutual locations of the focal point, imaged object area and film plane are relevant to the radiographic process. By contrast, the location of the virtual axis of rotation is solely related to the sweep velocity.

As an example of panoramic tomography apparatuses known in the art for dental radiography, reference is made to the FI patent 73091 (U.S. Pat. No. 4,741,007, correspondingly) and FI patent 853524 (U.S. Pat. No. 4,783,793, correspondingly), both filed by the applicant of the present patent.

Panoramic tomography apparatuses intended for dental radiography have mainly been used for radiographing the dental arch and the temporo-mandibular joints, or their condyles. It is a principal object of the present invention to further develop the apparatuses disclosed in the above-mentioned patents and the application filed by the applicant as well as other similar panoramic tomography apparatuses so that mandibular joint imaging projections of still greater versatility and higher diagnostic value become possible by means of simple accessories and/or arrangements without causing an essential increase in the price of the basic panoramic x-ray apparatus.

X-ray images taken from the temporo-mandibular joints are diagnostically a valuable source of information in a multitude of states of illness and pain. Imaging of the condyles is necessary in the diagnostics of a variety of problems encountered in oral surgery, biting disorders, straightening of teeth and malfunction of the temporo-mandibular joint. When exposing the temporo-mandibular joint in radiographic imaging, it is of extreme importance that the sharply imaging plane is both correctly positioned and correctly aligned so that the head of the condylar process and the mandibular fossa of the joint as well as the soft tissue between them can be imaged sharply and from a correct direction in order to reveal, for example, the degree of wear in the joint and its positional disorders.

The diagnostic value of radiographic images taken from temporo-mandibular area by means of conventional panoramic x-ray apparatuses is degraded through a non-optimal orientation of the x-ray beam during its sweep over the temporo-mandibular joint. This is related to the fact that, in order to attain a nondistorted image over the dental arch area, such an imaging geometry of panoramic x-ray apparatuses is preferred in which the x-ray beam passes through the mandible as perpendicularly as possible at the dental arch. In conventional apparatuses there is a corollary result that the requirement of perpendicularity cannot be fulfilled at the temporo-mandibular joint, or alternatively, its fulfillment would compel the use of such an imaging geometry in which the motion of the virtual axis of rotation at the condylar area is such in that the tomographic imaging effect is lost. Here, the situation approaches that of conventional radiography, which means that the whole of the patient's anatomy incorporated at the swept area is imaged on the film, whereby both temporo-mandibular joints, for example, become superimposed in the image.

It is a particular object of the invention to achieve such a narrow-beam tomographic method and such an apparatus which is based on a standard panoramic x-ray apparatus conventionally employed for imaging of dental structures, said apparatus being complemented in a novel and advantageous way with a new imaging mode in which the temporo-mandibular joints and structures adjacent thereof can be imaged with higher image quality and improved diagnostic value. Such a facility provides an essential improvement in the utility of conventional panoramic tomography apparatuses and makes investments in apparatuses more profitable and more justifiable for smaller health care units than before by virtue of the widened applicability of the apparatus. It is a further particular object of the invention to achieve such a method and apparatus, which permits, using standard panoramic x-ray apparatuses conventionally employed for imaging of dental structures, the imaging of both temporo-mandibular joints during a single exposure on a single film using mutually parallel imaging planes of the joints so that the imaging angle can be set within a certain sufficient range of angles employing simple implements to adjust the imaging angle optimal with respect to the imaged object area and the goal of imaging.

To achieve the goals described above and discussed later, the method according to the invention is principally characterized in that the speeds of the rotating motor and the film transfer motor in a frame part supporting the x-ray source and the film cassette are varied, or alternatively, the profiles of said speeds are set so that the shape of the sharply-imaging layers is appropriately contoured so as to make the mandibular joints coincide with the imaged layer irrespective of the position of the patient in the medial-sagittal plane.

Furthermore, the apparatus according to the invention is principally characterized in that said apparatus incorporates such motion control arrangements by which the arm connecting the x-ray source and the film cassette is pivotally rotatable and the film cassette is simultaneously transferrable using such speed profiles that both mandibular joints can be imaged on a single film in planes which are essentially parallel with the medial-sagittal plane of the patient.

The imaging mode of the mandibular joint condyles according to the invention can be adapted to conventional panoramic x-ray apparatuses by programming the logic control systems of motor drives to perform according to the above-mentioned imaging mode of mandibular joint condyles. The imaging mode of the mandibular joint condyles according to the invention requires no particular patient positioning and supporting arrangements, but rather the imaging angle of the mandibular joint can be varied in the horizontal plane by moving the patient in his medial-sagittal plane. The necessary adjustment members of patient positioning are generally already available in conventional panoramic x-ray apparatuses of standard equipping for optimal placement of the patient in a conventional panoramic x-ray exposure of the dental arches.

The method and apparatus according to the invention achieves a narrow-beam tomographic image of both temporo-mandibular joints on a single film during a single exposure from such an imaging angle that can be set through rapid and simple procedures optimal with respect to the goal of imaging.

The invention is next examined in greater detail by making reference to the figures of the attached drawing which illustrate diagrammatically a few exemplifying embodiments of the present invention, whereby the illustrating details must not be construed to limit the applications of the invention.

Figure 1:
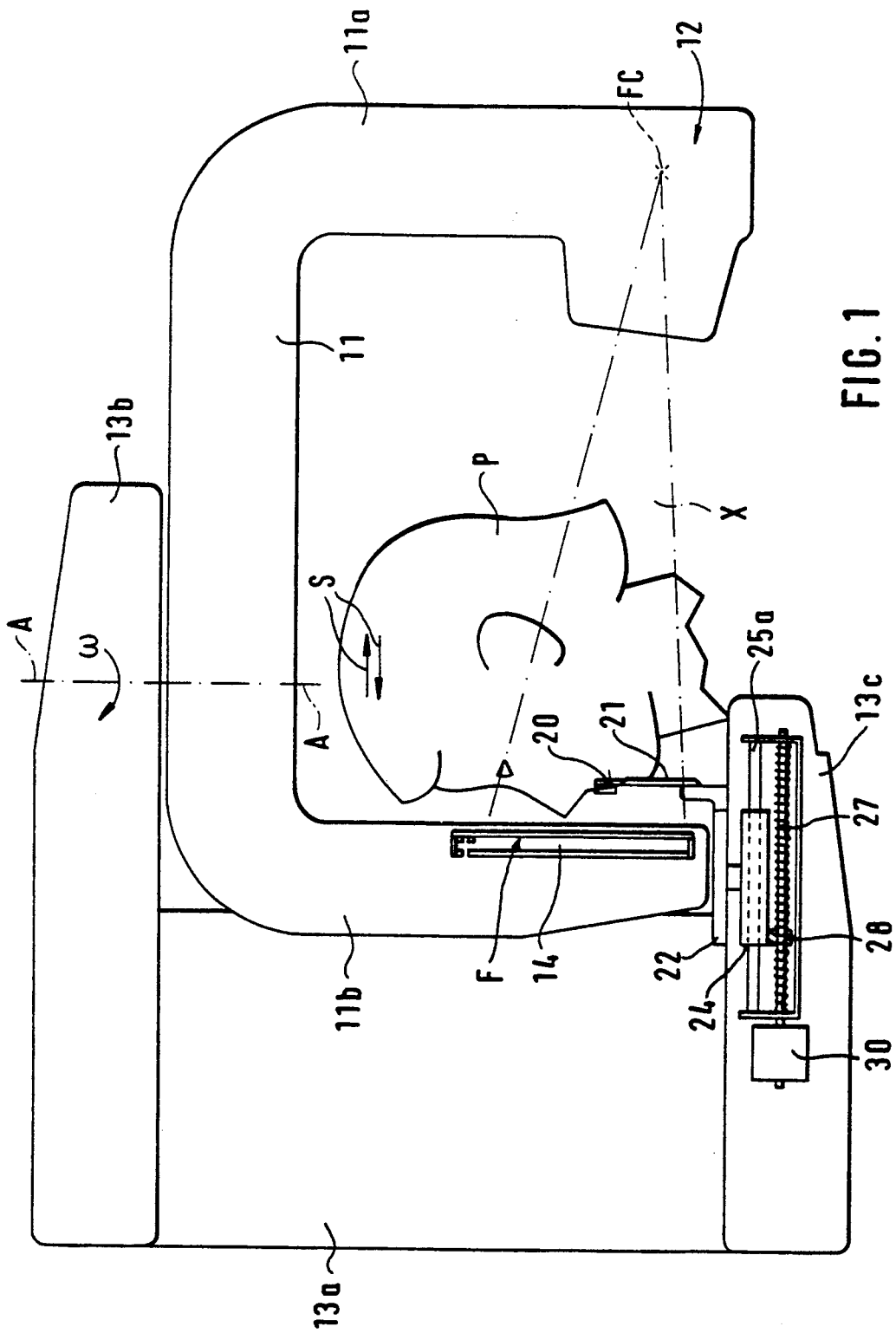
FIG. 1 shows diagrammatically in a side view a conventional panoramic radiographic apparatus of dental radiography with its patient positioning elements employed in conjunction with the present invention.
Figure 2:
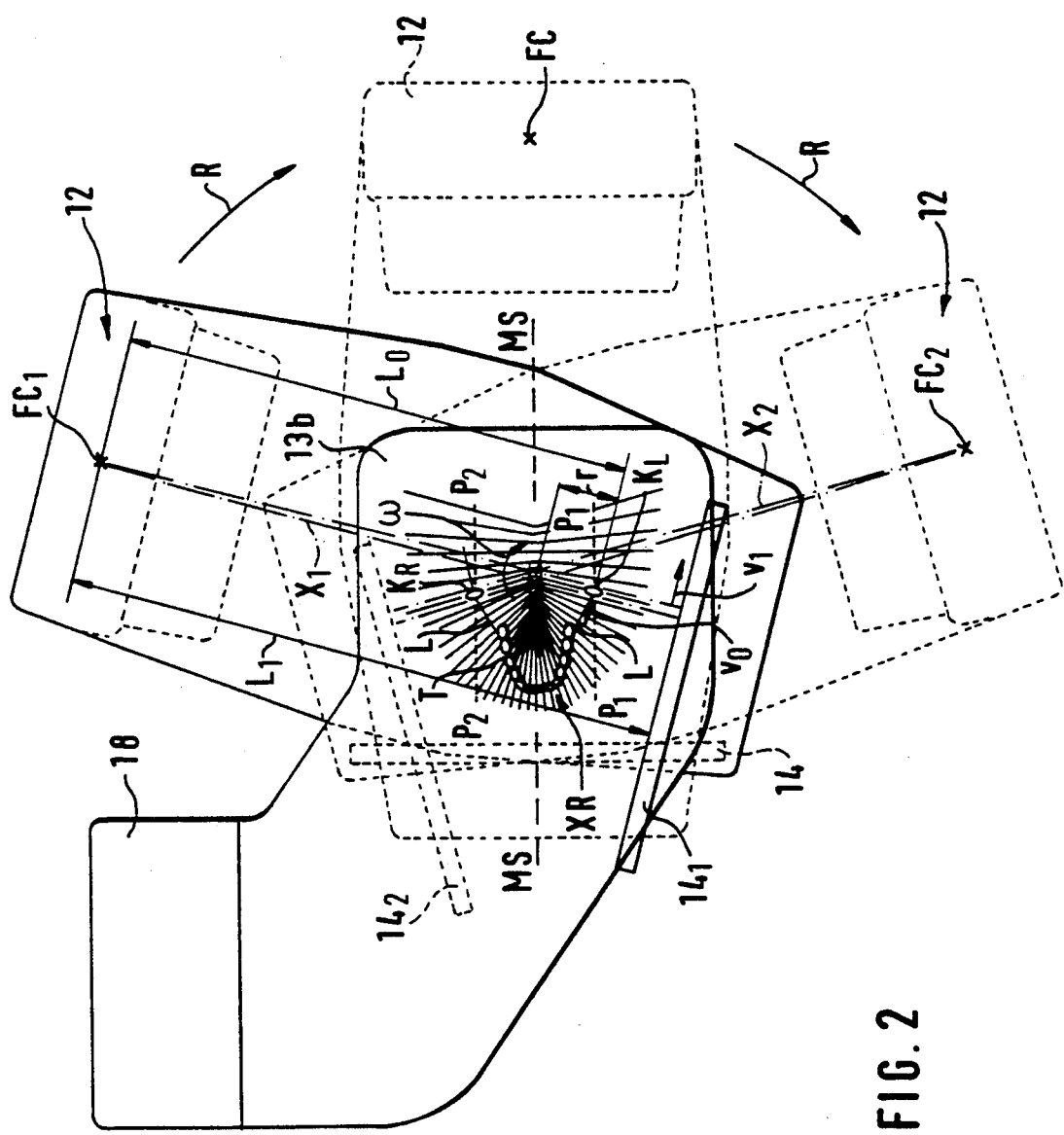
FIG. 2 shows the apparatus illustrated in FIG. 1 in a top view. Additionally shown in FIG. 2 are the essential system parameters related to the imaging geometry and the location of the temporo-mandibular joints to be imaged.
Figure 3A:
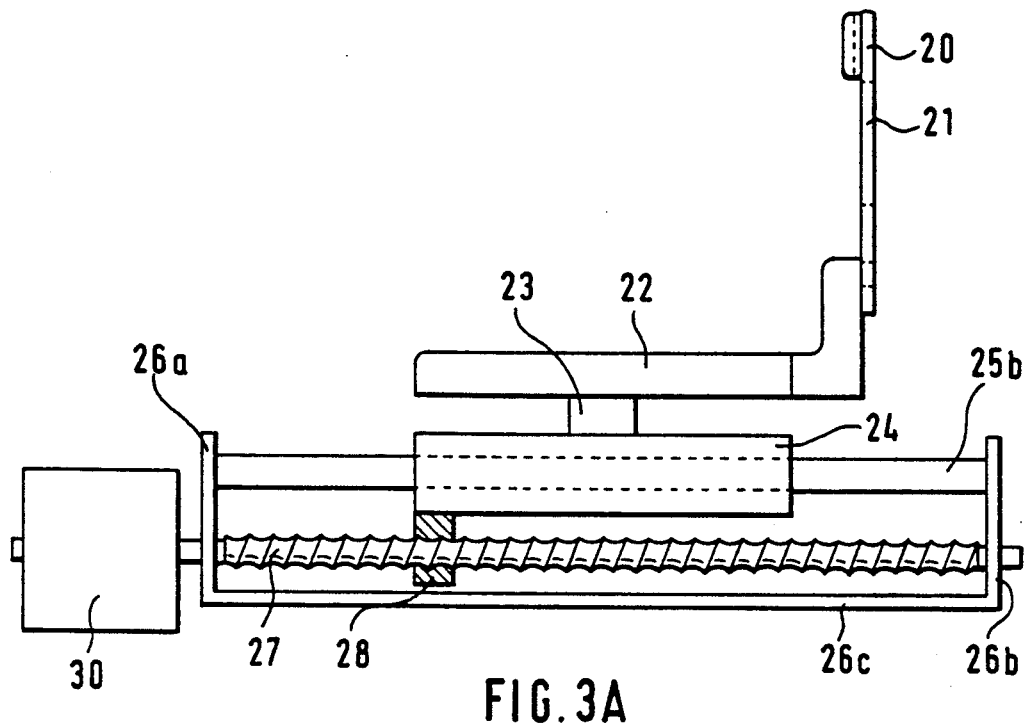
FIG. 3A shows a motor-actuated patient positioning mechanism in a side view.
Figure 3B:
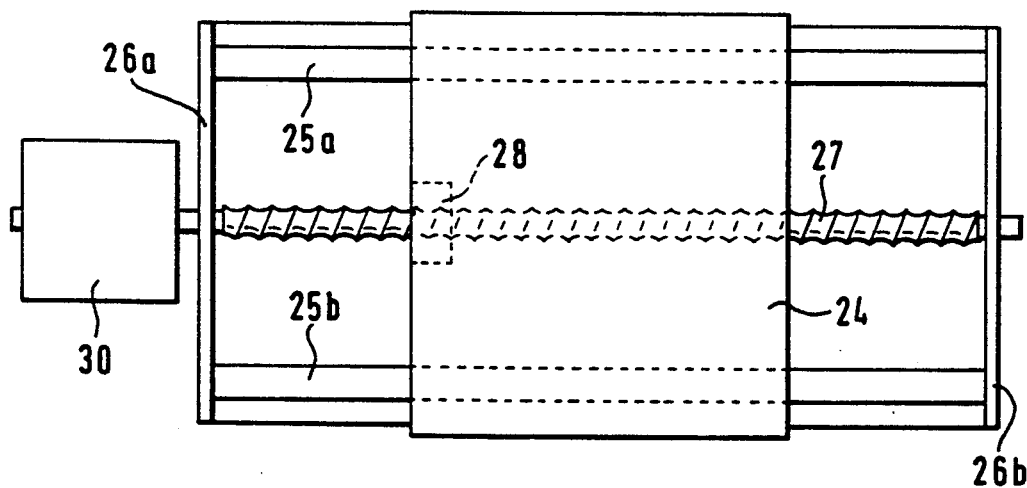
FIG. 3B shows the same mechanism as FIG. 3A in a top view.
Figure 4A:
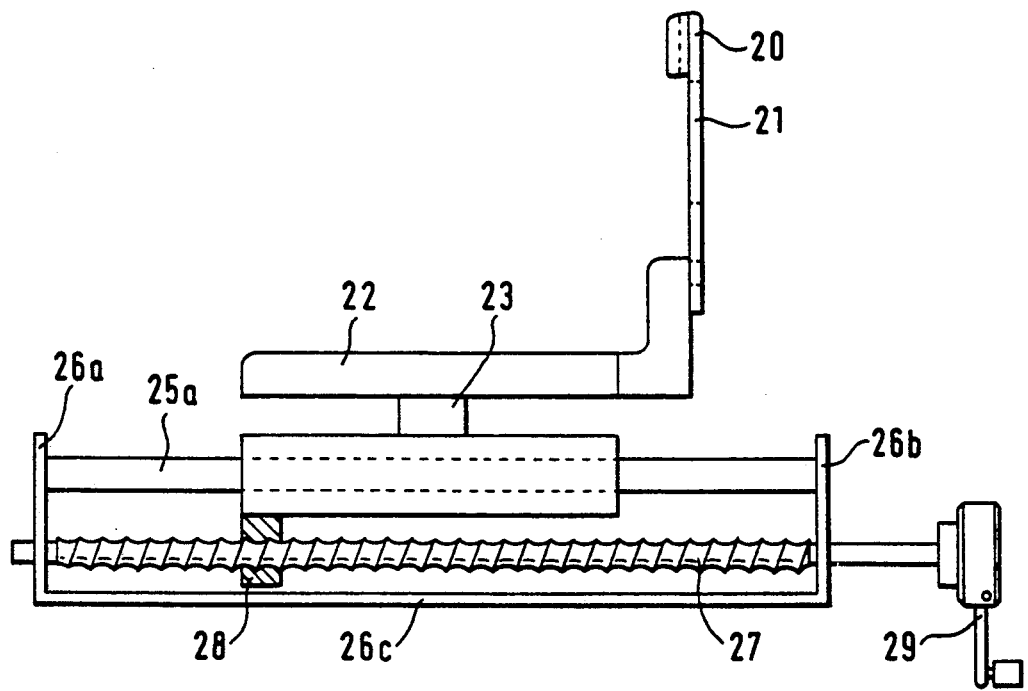
FIG. 4A shows a manually operated patient positioning mechanism in a similar view as that of FIG. 3A.
Figure 4B:
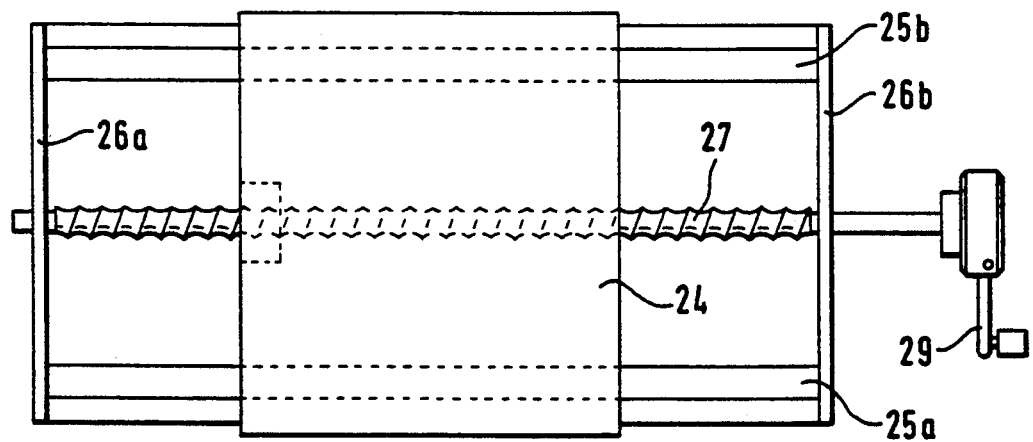
FIG. 4B shows the same mechanism as FIG. 4A in a top view.

According to FIGS. 1 and 2, the principal elements of a conventional panoramic radiographic apparatus applied to narrow-beam tomography comprises a so-called C-arm that incorporates a horizontal part 11 plus vertical parts 11a and 11b at its ends between which the patient P to be radiographed is placed. One vertical part 11a of the C-arm supports an x-ray source 12, while the other vertical part 11b carries an x-ray film cassette 14. The cassette 14 contains a film F onto which the narrow-beam panoramic image of the patient's dental structure is exposed. The film cassette 14 with its contained film F is arranged to be transferrable by means of a conventional motor actuator designated by reference number 32 in FIG. 7 simultaneously with the rotational motion of the C-arm about a nonstationary virtual vertical axis A—A at an angular velocity $\omega$ by means of a motor 31 shown in FIG. 7. During the exposure, the radiation is emitted from a focal point FC of the x-ray source 12 as a narrow beam X as illustrated in the horizontal section of FIG. 2.

In FIG. 2 the dental arch of the patient P is designated with reference L, the dental arch with reference T and the sections of the temporo-mandibular joints with references $K_R$ and $K_L$ and the patient's medial-sagittal plane with reference MS.

According to FIG. 2, the instantaneous imaging in the novel imaging mode according to the present invention takes place in mutually parallel planes $(P_1 \ldots P_1, P_2 \ldots P_2)$ intersecting the mandibular joints $K_R$ and $K_L$ of the patient P as described by the basic formula of panoramic radiography given below:

$$v_1/v_0 = L_1/L_0$$

$v_0 = \omega \cdot r$, where $L_0$ = distance from focal point FC to the instantaneously imaged point of the layer being imaged $L_1$ = distance from focal point FC to the film plane $\omega$ = angular velocity of rotational motion about the virtual axis of rotation $r$ = distance of imaged point from the virtual axis of rotation $R_0$ of the rotational motion $v_1$ = velocity of image point on the image or film plane.

During the imaging of the mandibular joints K in the imaging mode of the mandibular joint condyles according to the invention as illustrated in FIG. 2, the C-arm 11 has started its motion and reached a position in which the cassette 14 is in the position $14_1$ and the focal point of the x-ray beam reached the position $FC_1$, from which an x-ray beam $X_1$ is aimed to the center of the left mandibular joint $K_L$, whereby said mandibular joint $K_L$ becomes sharply imaged in the plane $P_1 \ldots P_1$, whose distance is r from the virtual axis of rotation $R_0$. Next, the C-arm continues its motion in the direction of the arrow R via the position shown in dashed line to a position in which the focus of the x-ray source 12 is in the position $FC_2$, whereby the x-ray beam is aligned to the right mandibular joint $K_R$, whereby the right mandibular joint $K_R$ becomes sharply imaged in the plane $P_2 \ldots P_2$. Then, the x-ray film cassette is in the position $14_2$.

In the embodiment of the present invention, the layers imaged in the planes $P_1 \ldots P_1$, $P_2 \ldots P_2$ passing through the mandibular joints $K_L$ and $K_R$ are aligned planar and mutually parallel by virtue of an appropriate program-controlled realization of the speeds $v_R$ and $v_1$ of the C-arm rotating motor 31 and the film transfer motor 32 in the manner to be described later in detail in conjunction with the description of FIGS. 6A, 6B and 7 so as to keep the above-described imaging condition $v_1/v_0 = L_1/L_0$ valid.

Figure 5A:
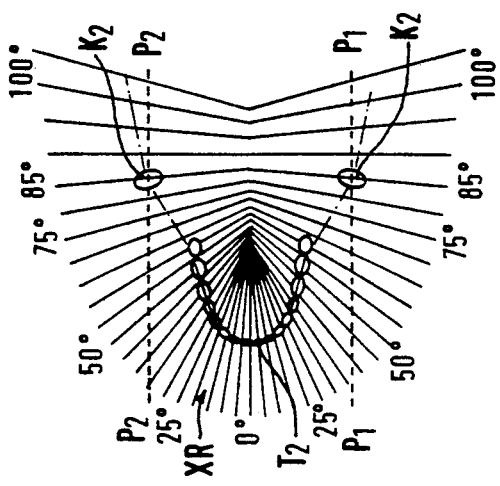
FIGS. 5A, 5B, 5C and 5D show the geometry of the dental arch and the temporo-mandibular joints to be imaged in the x-ray field for different imaging angles of the mandibular joints.

FIGS. 3A, 3B and 4A, 4B illustrate the mechanisms by which the patient P can be placed in his/her medial-sagittal plane MS in the direction of arrow S shown in FIG. 1 to such a position in which both mandibular joints $K_R$ and $K_L$ can be imaged on a single film during a single exposure in preset imaging angles to be discussed later in conjunction with FIGS. 5A ... 5D. The positioning mechanism of the patient P comprises at the upper end of an arm 21 a lip support 20 on which the upper lip of the patient P can rest so that the exposure can be performed both with an open and closed mouth of the patient P. The arm 21 is attached at its lower end to an L-arm 22, whose lower side is attached via a member 23 to a guided slide 24. Said slide is transferrable along horizontal guides 25a and 25b by means of a transfer screw 27. The transfer screw 27 is mounted in bearings between end members 26a and 26b of the transfer mechanism, said members also having the guides 25a and 25b attached to them. The glide block 24 has a nut element 28 attached to it, preferably a ball circulating nut running on the thread of the transfer screw 24. According to FIGS. 3A and 3B, the transfer screw is driven by a stepper motor 30 driven by circuit 33.

Figure 5B:
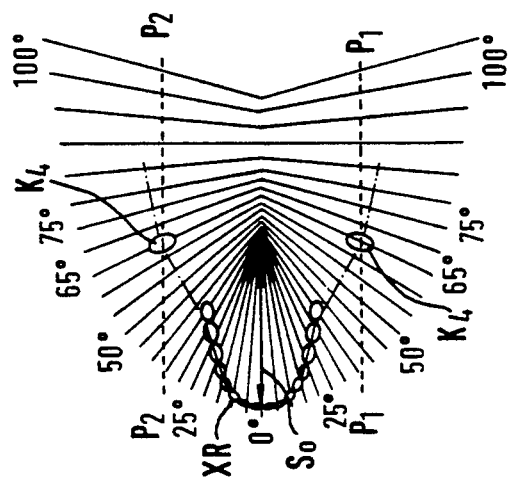
Figure 5C:
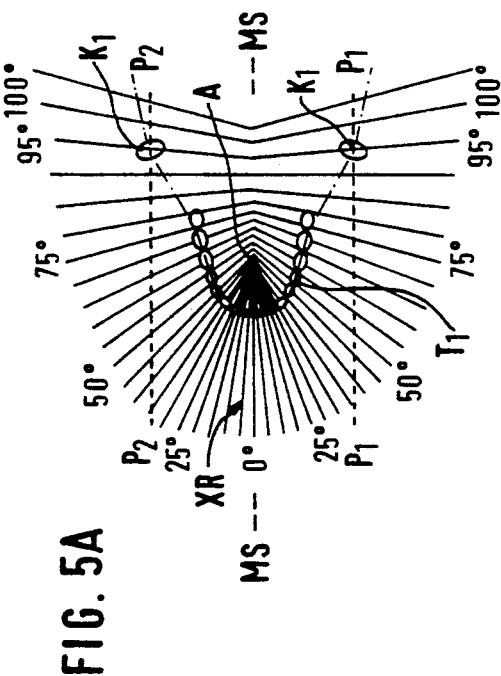
Figure 5D:
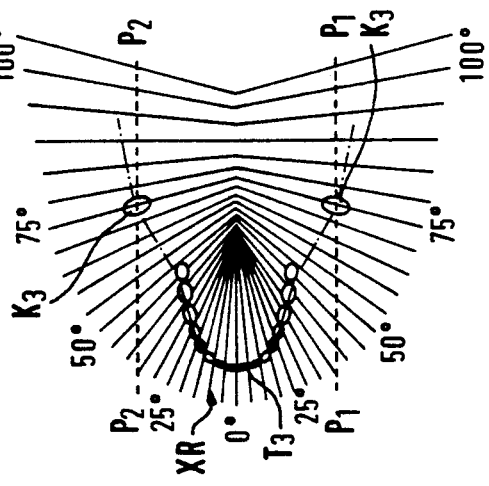

The above-described patient positioning mechanisms are employed in both imaging modes of the panoramic x-ray apparatus, that is, in both the normal (first) imaging mode in which x-ray imaging is performed over the entire dental arch and the imaging mode (second) according to the invention in which imaging is performed at both temporo-mandibular joints $K_L$ and $K_R$ on a single film F from an angle which is adjustable to a preset value by means of the adjustment mechanism described above. The location of the dental arch and the mandibular joints K to be imaged is shown in FIGS. 5A, 5B, 5C and 5D in an x-ray field (angle scales 0° ... 100°, angle 0° = medial-sagittal plane MS of the patient P) when the patient is set to different positions by means of mechanisms shown in FIGS. 3A, 3B or 4A, 4B. According to FIG. 5A, the temporo-mandibular joints K are imaged in the planes $P_1 \ldots P_1$ and $P_2 \ldots P_2$ from an angle of 95°. In FIG. 5B the patient P has been moved forward, that is, toward the film cassette 14 so that the mandibular joints $K_2$ are imaged from an angle of 85°. In FIG. 5C the patient has further been moved forward so that the mandibular joints $K_3$ are imaged from an angle of 85° and the forward transfer identified in the diagram relative to the initial position indicated in FIG. 5D are in this example maximally = $S_0$, whereby the mandibular joints $K_4$ are imaged in an angle of 65°. In typical applications the range of 55° ... 95° is sufficient and possible so that the transfer distance $S_0$ of the patient still remains within such boundaries which avoid the collision of the film cassette 14 with the patient P.

Figure 6A:
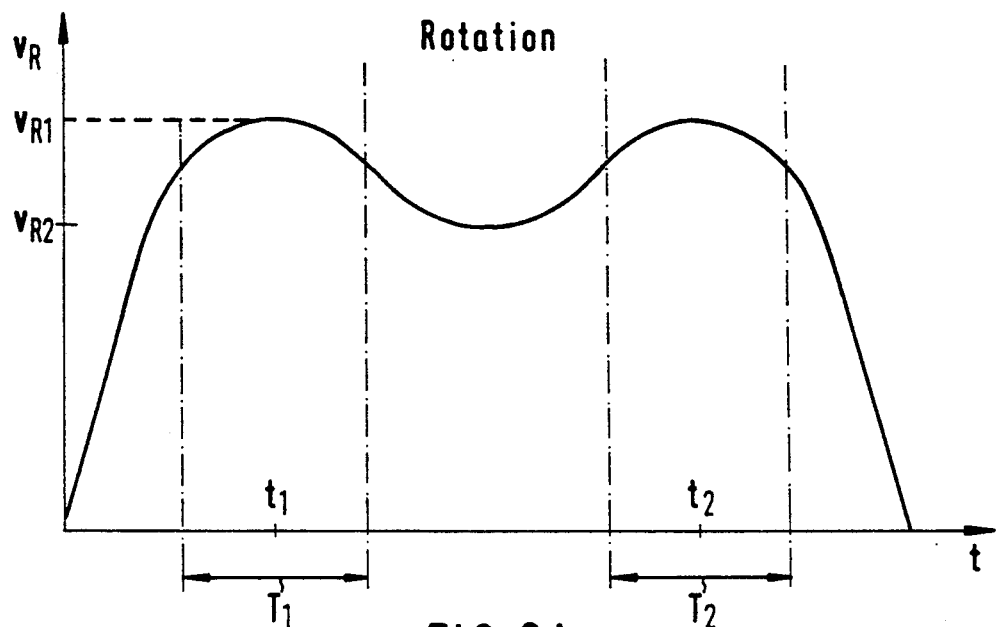
FIG. 6A shows in a graphic form the rotational speed profile of the x-ray beam as a function of time during the imaging of the temporo-mandibular joint according to the invention.
Figure 6B:
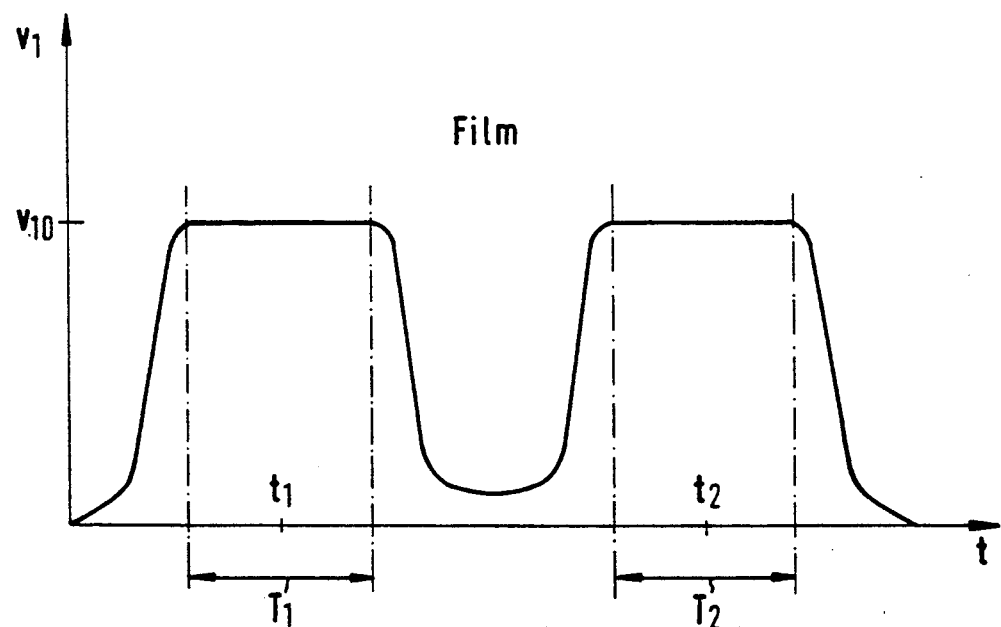
FIG. 6B shows similarly to FIG. 6A the film travel speed profile during the imaging of the temporo-mandibular joint according to the invention when the rotational speed profile is that illustrated in FIG. 6A.
Figure 7:
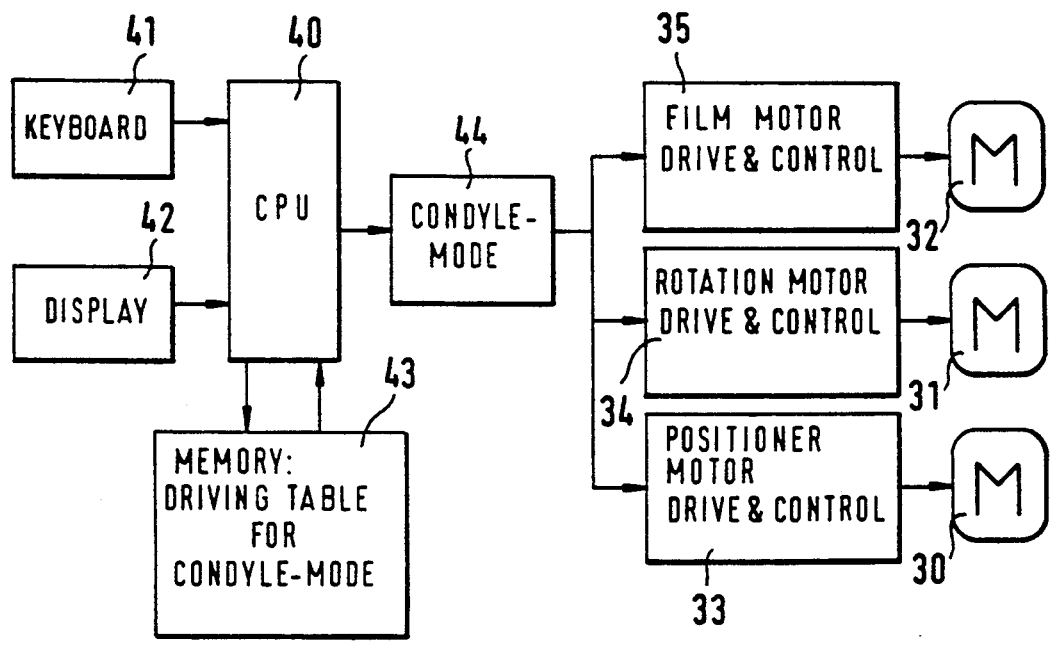
FIG. 7 shows the block diagram of the control system employed in the method and apparatus according to the invention.

In FIGS. 6A and 6B is shown the rotational speed $v_R$ of the C-arm corresponding to the angular velocity $\omega$ and the film travel speed $v_1$ indicated in the diagram of FIG. 2 as a function of time t. The rotation of the C-arm about a pivotal axis A—A is commenced from a home position by means of a motor 31 shown in FIG. 7 when the mandibular joints are imaged in the novel imaging mode according to the invention. Here, the rotational speed of the C-arm as well as film travel speed $v_1$ are first ramped in an essentially linear manner according to the diagram of FIG. 6. According to FIGS. 6A and 6B, the area of the left mandibular joint $K_L$, for example, is first imaged during the time interval $T_1$ so that the C-arm is at time instant $t_1$ in a position corresponding to the position $FC_1$ of the x-ray source focal point indicated in FIG. 2. During the imaging of the first mandibular joint $K_L$ the film travel speed is kept constant = $v_{10}$. Then, after the imaging of the first mandibular joint $K_L$ is ready, the rotational speed $v_R$ (having a maximum value of $v_{R1}$) is reduced down to a minimum value $v_{R2}$ and the film travel speed $v_1$ is reduced by a relatively greater value, after which the imaging operation proceeds to the object area of the second mandibular joint $K_R$, which is covered during the time interval $T_2$. At time instant $t_2$ the C-arm is in the position indicated by dashed line in the diagram of FIG. 2, where the focal point of the x-ray source is indicated by $FC_2$. When also the imaging of the second mandibular joint $K_R$ is completed, both the rotational speed $v_R$ and the film travel speed $v_1$ are brought down to zero in the manner shown in FIGS. 6A and 6B, whereby the simultaneous imaging of both temporo-mandibular joints $K_L$ and $K_R$ on a single film F is completed. The speed profiles of the rotational speed $v_R$ and the film travel speed $v_1$ described above in conjunction with the explanation of FIGS. 6A and 6B are achieved by means of a control system illustrated in FIG. 7, whereby said control system is also applicable during the normal panoramic imaging mode of the dental arch. The control system comprises a central unit 40 with a keyboard 41 and a display 42 attached to it. Connected to the central unit 40 is a memory 43 containing the speed profile tables of the motors 30,31,32. When operating in the novel imaging mode of the mandibular condyles according to the invention, the central unit 40 is connected via a sequencing unit 44 of the mandibular joint imaging mode to driver circuits 33, 34 and 35 of the motors 30, 31 and 32. At the start of mandibular joint imaging, the apparatus is controlled from the keyboard 41 into the mandibular joint imaging mode, whereby the sequencing unit 44 of the mandibular imaging mode is activated. Using the keyboard 41, the imaging angle is entered, whereby its value can be varied according to FIGS. 5A ... 5D in the range 65° ... 95°, for example. The display 42 indicates the imagining angle and the central unit 40 fetches the speed profile tables corresponding to the selected imaging angle of the mandibular imaging mode from the memory 43. The central unit 40 controls via the sequencing unit 44 of the mandibular imaging mode first the motor 30 so that patient positioning mechanism 20,21 is transferred to a position corresponding to the imaging mode entered from the keyboard 41. When the mandibular imaging operation is started after this under control from the keyboard, the central unit 40 controls with the help of the speed profile tables fetched from the memory 43 the motors 31 and 32 so that the speed profiles $v_R(t)$ and $v_1(t)$ shown in FIGS. 6A and 6B are implemented.

Whereas only such an embodiment of the invention is described above in which the rotational speed $v_R$ and the film travel speed $v_1$ are varied under program control in both the panoramic imaging mode and the novel mandibular joint imaging mode, the invention also concerns such applications in which said control is implemented by mechanical means in either or both imaging modes, whereby such a rotating mechanism of the C-arm 11 is possible, for example, as is disclosed in the FI patent 73091 (U.S. Pat. No. 4,741,007, correspondingly). The claims of the patent application are presented in the following, whereby the different details of the invention may be varied and deviated within the scope of the claims which define the invention from those of the exemplifying embodiments.

I claim:

1. A method of narrow-beam tomography utilizing an x-ray source (12) whose narrow x-ray beam (X) is aimed to pass through the object area to be radiographed onto a movable x-ray film (F), wherein the object area to be radiographed in the patient (P) is kept stationary in a certain preset position while the x-ray source (12) is rotated in a fixed plane about a virtual axis of rotation ($R_0$) and a film cassette (14) is simultaneously moved, and wherein according to a first operating mode the patient (P) is supported by patient positioning means (20 . . . 30) for exposing panoramic radiographic images of the dental arch (L) so that the sharply imaging plane is located between the virtual axis of rotation of the x-ray beam and the film plane, and wherein in addition to the first operating mode the panoramic tomography x-ray apparatus is set to a specific exposure mode for imaging the mandibular joint and the patient is positioned in the panoramic x-ray apparatus with the help of the above-mentioned patient positioning means (20 . . . 30), comprising the steps of:

setting the sharply imaging layer in the mandibular joint imaging mode to coincide with vertically aligned planes ($P_1$ . . . $P_1$, $P_2$ . . . $P_2$) which are substantially parallel to the medial-sagital plane (MS) of the patient (P) and pass through the condyles of the mandibular joints;

prior to commencement of the mandibular joint imaging mode, transferring the positioning means (20 . . . 30) of the patient (P) in the forward-backward position (S) to select the imaging angle from which the x-ray beam is aimed through the condyles (R) of the mandibular joints; and then controlling the speeds ($V_R$) of a motor (31) rotating a frame part supporting the x-ray source (12) and ($V_1$) of the film cassette (14) so that the shape of the sharply-imaging layers imaged on the planes ($P_1 - P_1$, $P_2 - P_2$) is appropriately contoured so as to make the mandibular joints (K) coincide with the imaged layer irrespective of the position of the patient in the medial-sagital plane (MS).

2. A method as in claim 1, comprising the step of controlling the speeds by looking up speed profiles of the rotating motor (31) and the film transfer motor (35) in speed profile tables stored in a memory (43) of a central processing unit (40) associated with a control system of the x-ray apparatus.

3. A method as defined in claim 1, comprising the step of controlling the speed of the rotating motor (31) and the film transfer motor (35) using speed profile tables stored in a memory (43) of a central processing unit (40) of a control system of the apparatus.

4. A method as defined in claim 1, wherein the steps of transferring the positioning means (20 . . . 24) of the patient (P) comprises the step of controlling driver circuits (33) of a central processing unit (40) in a control system operatively associated with the panoramic tomography apparatus so as to control the operation of a motor (30) coupled to the positioning means.

5. A panoramic tomographic apparatus for dental radiography, said apparatus comprising a body part (13b) to which is mounted an arm (11, 11a, 11b) pivotal in bearings about a vertical axis (A—A), the arm having one end carrying an x-ray tube (12) and the other end carrying a film cassette (14) capable of housing an x-ray film (F), the space between said x-ray tube (12) and said film cassette (14) being able to accommodate the object area to be radiographed in the patient (P), and said apparatus further comprising actuating means capable of rotating said pivotally mounted arm (11, 11a, 11b) in the horizontal plane and transferring said film cassette (14) simultaneously for exposing a panoramic radiographic image, and patient positioning means (20, 21) transferable manually or by a motor (30) in the forward-backward direction for positioning the patient (P) in such a position that, in the specific mandibular joint imaging mode, permits the imaging of the mandibular joint, and the improvement comprising:

means controlling the rotational speed ($V_R(t)$) of the arm and simultaneously controlling the transfer speed ($V_1(t)$) of the film cassette so that both mandibular joints of the patient are imaged on a single film (F) in planes that are substantially parallel with the medial-sagital plane (MS) of the patient; and means operative to position the patient positioning means so that the angle to the medial-sagital plane (MS) of the patient at which the x-ray beam (X) intersects the condyles of the mandibular joints is selectable in the range of substantially 55° . . . 95°.

6. An apparatus as defined in claim 5, wherein:

said patient positioning means comprises a transfer screw (27) and an element driven by a motor (30) for transferring the patient positioning means (20, 21) in the forward-backward direction (S)

a driver circuit (33) operatively associated with said motor (30); and the driver circuit being controllable by a central processing unit (40) of the panoramic x-ray apparatus.

7. An apparatus as defined in claim 6, further comprising:

a control unit which incorporates a central processing unit (40) with an attached keyboard (41) and a display (42);

a motor (31) for rotating the arm;

a film transfer motor (32) for controlling the transfer of the film cassette;

said central processing unit (40) being connected to a memory unit (43) that contains speed profile tables of the different motors (30, 31, 32) of the apparatus for both said imaging modes; and the central processing unit being operative to control the speeds ($v_R$, $v_1$) of the rotating motor (31) and the film transfer motor (32) in both the conventional panoramic imaging mode occurring along a contour conforming to the dental arch and the mandibular joint imaging profile, in response to the speed profile tables.

* * * * *